United States Patent
Treado et al.

(10) Patent No.: US 10,779,713 B2
(45) Date of Patent: Sep. 22, 2020

(54) MOLECULAR CHEMICAL IMAGING ENDOSCOPIC IMAGING SYSTEMS

(71) Applicant: ChemImage Corporation, Pittsburgh, PA (US)

(72) Inventors: Patrick Treado, Pittsburgh, PA (US); Matthew Nelson, Pittsburgh, PA (US); Shona Stewart, Pittsburgh, PA (US)

(73) Assignee: CHEMIMAGE CORPORATION, Pittsburgh, PA (US)

( * ) Notice: Subject to any disclaimer, the term of this patent is extended or adjusted under 35 U.S.C. 154(b) by 323 days.

(21) Appl. No.: 15/932,435

(22) Filed: Dec. 9, 2015

(65) Prior Publication Data

US 2018/0263475 A1 Sep. 20, 2018

Related U.S. Application Data

(60) Provisional application No. 62/089,777, filed on Dec. 9, 2014, provisional application No. 62/113,958, filed on Feb. 9, 2015.

(51) Int. Cl.

| *A61B 1/07* | (2006.01) |
|---|---|
| *A61B 1/04* | (2006.01) |
| *A61B 1/06* | (2006.01) |
| *A61B 1/307* | (2006.01) |
| *A61B 1/00* | (2006.01) |

(52) U.S. Cl.
CPC .......... *A61B 1/043* (2013.01); *A61B 1/00009* (2013.01); *A61B 1/00186* (2013.01);
(Continued)

(58) Field of Classification Search
CPC .......... A61B 1/07; A61B 1/042; A61B 1/043; A61B 1/063; A61B 1/0646; A61B 1/0653;
(Continued)

(56) References Cited

U.S. PATENT DOCUMENTS 8,167,794 B2 * 5/2012 Matsumoto ............ A61B 1/041
600/160
9,041,932 B2 5/2015 Priore et al.
(Continued)

FOREIGN PATENT DOCUMENTS

WO 01/50955 A1 7/2001

OTHER PUBLICATIONS

Wang et al., "Three-Dimensional Imaging of Ureter With Endoscopic Optical Coherence Tomography", NIH Public Access Author Manuscript published in final edited form as: Urology, May 2011; 77(5): 1254-1258. (Year: 2011).*
(Continued)

*Primary Examiner* — William C Vaughn, Jr.
*Assistant Examiner* — Joseph Daniel A Towe
(74) *Attorney, Agent, or Firm* — Pepper Hamilton LLP

(57) ABSTRACT

The instant disclosure provides for medical imaging systems that may be used in conjunction with an intraoperative medical device, such as an endoscope. Generally, the disclosed medical imaging systems include an illumination source configured to generate illuminating photons for illuminating a biological sample. An optical signal modulator is configured to separate one or more of the illuminating photons and photons that have interacted with the biological sample into a first optical signal having first multi-passband wavelengths and a second optical signal having second multi-passband wavelengths. At least one detector is configured to detect one or more of the first optical signal and the second optical signal and generate at least one image data set. A processor is configured to analyze the at least one image data set. In some embodiments, the processor is configured to differentiate between structures of the biological sample, such as between an ureter and surrounding tissue.

46 Claims, 16 Drawing Sheets

(52) U.S. Cl.
CPC ............ *A61B 1/063* (2013.01); *A61B 1/0607* (2013.01); *A61B 1/0646* (2013.01); *A61B 1/0653* (2013.01); *A61B 1/0684* (2013.01); *A61B 1/07* (2013.01); *A61B 1/307* (2013.01); A61B 1/00096 (2013.01); A61B 1/042 (2013.01)

(58) Field of Classification Search
CPC ... A61B 1/0684; A61B 1/307; A61B 1/00009; A61B 1/00096
USPC .......................................................... 348/68
See application file for complete search history.

(56) References Cited

U.S. PATENT DOCUMENTS

| | | | |
|---|---|---|---|
| 2002/0016533 A1 | 2/2002 | Marchitto et al. | |
| 2012/0083678 A1* | 4/2012 | Drauch ................ | A61B 5/0075 600/310 |
| 2013/0176568 A1* | 7/2013 | Priore .................. | G01N 21/255 356/416 |
| 2015/0198793 A1 | 7/2015 | Kosanic et al. | |
| 2016/0213252 A1* | 7/2016 | Hillman ............. | G02B 23/2476 |
| 2018/0116494 A1 | 5/2018 | Treado et al. | |

OTHER PUBLICATIONS

Wang et al. Three-Dimensional Imaging of Ureter with Endoscopic Optical Coherence Tomography, Urology, Jan. 22, 2012, vol. 77(5):1254-1258.
International Search Report and Written Opinion for PCT/US2018/030155 dated Jul. 9, 2018.

\* cited by examiner

MOLECULAR CHEMICAL IMAGING ENDOSCOPIC IMAGING SYSTEMS

CROSS-REFERENCE TO RELATED APPLICATIONS

This application claims benefit of and priority to U.S. Provisional Patent Application No. 62/089,777 entitled "Molecular Chemical Imaging Endoscopic Imaging Systems," filed Dec. 9, 2014, the disclosure of which is incorporated by reference herein in its entirety. This application further claims benefit of and priority to U.S. Provisional Patent Application No. 62/113,958 entitled "Molecular Chemical Imaging Endoscopic Imaging Systems," filed Feb. 9, 2015, the disclosure of which is incorporated by reference herein in its entirety.

BACKGROUND

In performing surgery on the human body, it is essential that surgeons do not accidentally cut or otherwise harm organs, passages or other anatomical structures such as the urethra and ureter. The presence of blood, fat, arteries, veins, intervening tissue such as muscle and fascia and other highly scattering and absorbing media can make it extremely difficult to locate with great accuracy such organs, passages and anatomical structures in the immediate vicinity of the surgical site. Light emitting catheters have been used to detect irregularities in a duct, vessel or organ to assist a surgeon in locating anatomical structures of interest to permit the proper performance of the surgical procedure. However, there exists a need for improved intraoperative imaging tools which are capable of real-time detection of anatomical structures in assisting surgeons performing delicate operations without harming tissue surrounding the surgical site.

SUMMARY OF THE DISCLOSURE

The instant disclosure provides medical imaging systems. The medical imaging systems may be used in conjunction with an endoscope. Generally, the medical imaging system includes an illumination source configured to generate illuminating photons. The illuminating photons are transmitted to one or more filters configured to filter a first plurality of illuminating photons and generate a first plurality of filtered photons comprising a first passband wavelength and a second plurality of filtered photons comprising a second passband wavelength. A sample is then illuminated with the first plurality of filtered photons and the second plurality of filtered photons to generate a first plurality of interacted photons and a second plurality of interacted photons. One or more detectors are configured to detect the first plurality of interacted photons and the second plurality of interacted photons and generate one or more image data sets.

In another embodiment, the imaging system includes an illumination source configured to illuminate a sample and generate interacted photons. One or more filters are configured to filter one or more of a first plurality of the interacted photons and transmit a first passband wavelength and a second plurality of the interacted photons and transmit a second passband wavelength. The first and second passband wavelengths are transmitted to one or more detectors configured to detect the first passband wavelength and the second passband wavelength and generate one or more image data sets.

In yet another embodiment, the imaging system features an illumination source configured to illuminate a sample with one or more of a first plurality of illuminating photons having a first wavelength to generate a first plurality of interacted photons and a second plurality of illuminating photons having a second wavelength to generate a second plurality of interacted photons. One or more detectors are configured to detect the first plurality of interacted photons and the second plurality of interacted photons to generate one or more image data sets.

DETAILED DESCRIPTION

Figure 1:
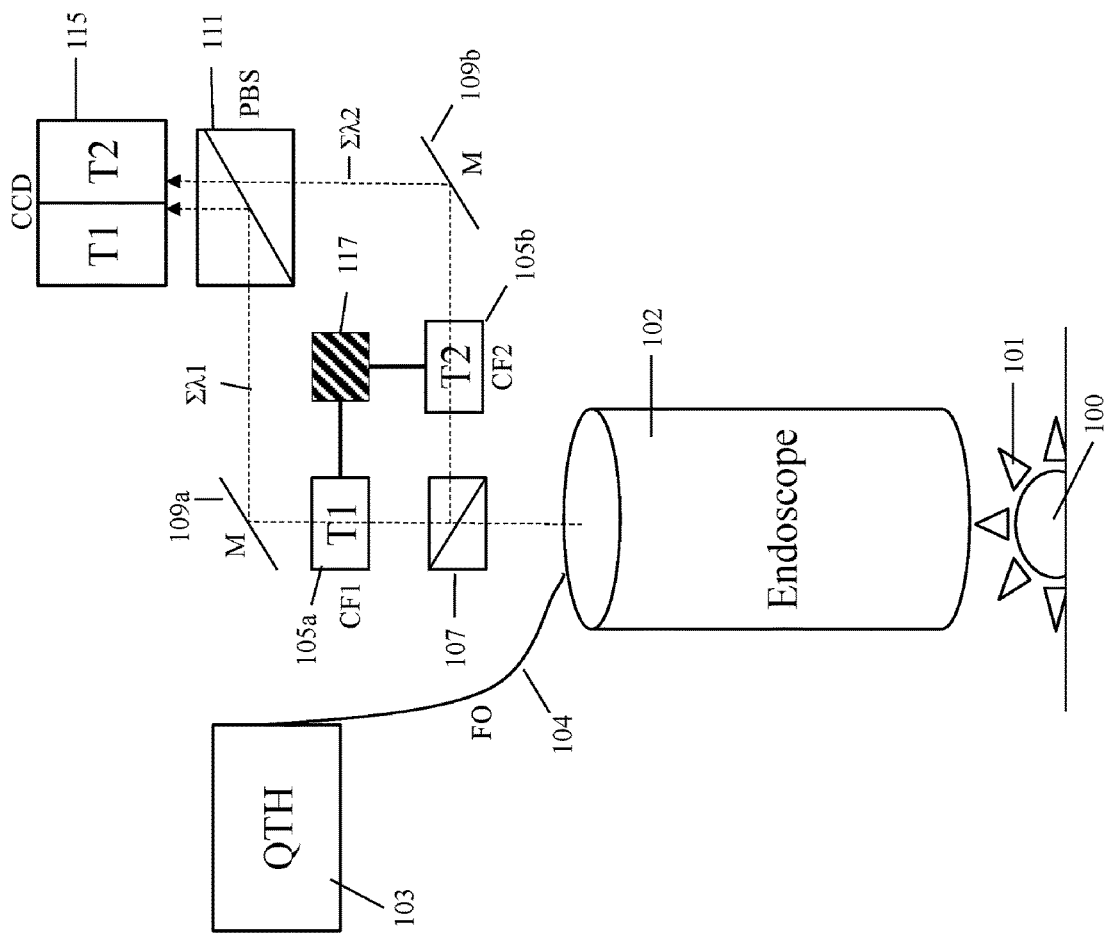
FIG. 1 illustrates an endoscope comprising an imaging system having a plurality of conformal filters in a dual polarization configuration, according to an embodiment.

The present disclosure features intraoperative medical imaging systems which can assist surgeons in various medical procedures. The systems disclosed herein are suitable for use as stand-alone devices, or may be incorporated into other medical imaging devices such as a robotic platform. In one embodiment, the systems disclosed herein may be used in conjunction with an endoscope. The medical imaging systems disclosed herein may provide real-time detection of tumors and anatomic structures during endoscopic procedures. Generally, the systems disclosed herein provide illuminating a biological sample, collecting photons that have interacted with the sample, detecting the interacted photons to generate an image data set of the sample, and analyzing the image data set. Interacted photons may comprise one or more of photons absorbed by a sample, photons reflected by a sample, photons scattered by a sample, and photons emitted by a sample. In one embodiment, the medical imaging system provides multivariate imaging. Multivariate imaging features generating two or more wavelengths corresponding to a first image data set (T1) and a second image data set (T2). These first and second image data sets may be analyzed using an optical computation. Multivariate imaging creates enhanced image contrast and increased discrimination between a target and background. In certain embodiments, the first image data set and the second image data set feature hyperspectral image data. In another embodiment, the medical imaging systems feature imaging frame rates of >10 Hz (hyper-cubes/second).

The systems disclosed herein may be used on various biological samples, such as tissues, organs, anatomical structures, physiological systems, cells, blood, fat, nerves, muscle and the like. In certain embodiments, the systems may be employed in various areas of the body, which would be apparent to one of skill in the art in view of this disclosure. For example, the systems might be employed to investigate and/or perform surgery in the gastrointestinal tract. In such an application, the systems may be employed in any of the esophagus, the stomach, the duodenum, the small intestine, the large intestine/colon, the bile duct, the rectum, the anus and the like. The systems may further be employed on structures of the respiratory tract including, without limitation, the nose, the sinuses and the lower respiratory tract. In other embodiments, the systems disclosed herein may be used to investigate and/or perform surgery on structures comprising the urinary tract, such as the bladder, ureter, kidneys and so forth. In yet other embodiments, the systems may be employed on structures comprising the female reproductive system, such as the cervix, uterus, fallopian tubes and the like. Further, the systems may be employed in medical procedures performed during pregnancy, such as to investigate and/or perform medical procedures on the amnion and fetus. In another embodiment, the systems described herein may be employed to investigate and/or perform surgery on the structures involving the musculoskeletal system, i.e., orthopaedics, including the structures of the hand, the knee, the elbow, the shoulder, the spine, including the epidural cavity, bursae, muscles, ligaments, connective tissues and the like.

Further, the systems may be configured to discriminate between two or more different biological samples. For example, the systems disclosed herein may be configured to discriminate between a ureter and surrounding tissue and fat. In one embodiment, the systems disclosed herein may be employed to differentiate cancer from normal tissue, determine one or more of a cancer stage, cancer progression and cancer grade. In another embodiment, the systems may be employed during surgical procedures to remove cancer tissue or tumors found on the biological sample. In yet another embodiment, the systems described herein may be employed to differentiate anatomical structures by identifying a bodily fluid associated with such anatomic structures. Bodily fluids may include, for example, urine, saliva, sputum, blood, feces, mucus, pus, semen, lymph, wound exudate, mammary fluid, vaginal fluid and the like. Anatomical structures having an associated bodily fluid would be apparent to those of ordinary skill in the art. As disclosed herein, the systems of the present disclosure provide illumination to a biological tissue. It is known that such illumination may penetrate a biological sample up to several centimeters, depending on wavelength and tissue type. Thus, such illumination penetration permits the imaging of bodily fluids contained inside an anatomical structure. Further, the bodily fluids may be directly imaged where their presence resides outside of the anatomical structure or other biological sample. In another embodiment, the systems disclosed herein may be employed to identify a ureter by detecting urine in or around the ureter.

In another embodiment, the instant systems may be employed with the use of one or more contrasting-enhancing agents. Contrast-enhancing agents may include one or more stains or dyes. When only one stain or dye is used, the procedure is referred to as staining. Multiple staining comprises the use of more than one stain or dye. As used herein, a "stain" or "dye" is any chemical or biological compound that can bind to a substance in a biological sample, to induce a color. For example, a stain or dye can bind to a particular cellular or biochemical structure (e.g., cell membrane, organelles, nucleic acid, protein) to induce contrasts when viewed using the systems described herein. In some embodiments, the stain or dye can induce a color by emitting electromagnetic radiation at one or more wavelengths when excited (i.e., fluoresce).

The one or more stains or dyes can be used, for example, in vivo or ex vivo. In some embodiments, the stain or dye is any stain or dye suitable for use in a living organism/individual that does not kill cells, i.e., a biological stain. Examples of biological stains include, but are not limited to, azo dyes, arylmethane dyes, cyanine dyes, thiazine dyes, xanthene dyes (e.g., eosin), natural stains (e.g., alizarin red), steroids, trypan blue, janus green, indocyanine green, alizarin red, propidium iodide, erythrosine, 7-aminotinomycin D, and Nile blue. In one embodiment, the contrasting-enhancing agent is a fluorescent contrast-enhancing agent. In one embodiment, the contrast-enhancing agent may include a Flourophor. Suitable Fluorophores include an immuno-fluorescent compound, a basophilic compound, an acidophilic compound, neutral stains and naturally occurring luminescent molecules.

When one or more stains or dyes are used in conjunction with the systems and methods described herein, a user (e.g., a surgeon) can intra-operatively identify histology, pathology, morphology, position, chemicals, and chemical reactions in or around the biological sample. For example, some (one or more) biological stains can identify cancerous cells so that the surgeon can resect the tumor. Other biological stains can also identify living cells (tissue) versus non-living cells. Once the contrast-enhancing agent is applied to the biological sample, the sample can be irradiated with photons having a wavelength within the illumination wavelength range of the applied contrast-enhancing agent in order to obtain spectral images as set forth in the instant disclosure.

In another embodiment, the contrast-enhancing agent may be ingested by a subject, where the contrast-enhancing agent will appear in a bodily fluid. In one embodiment, the contrast-enhancing agent may be taken orally, through an IV or through other means as would be apparent to one of skill in the art in view of this disclosure. Once the contrast-enhancing agent is ingested, the target biological sample may be examined by the systems disclosed herein. The systems may be configured to detect the contrast-enhancing agent in the bodily fluid to provide contrast between structures comprising the bodily fluid and surrounding biological samples, such as surrounding tissue. For example, a patient may orally ingest a solution comprising a contrast-enhancing agent where the contrast-enhancing agent at a certain time thereafter appears in the patient's urine. A endoscopic procedure may be performed on the kidney area of the patient with a system according to the instant disclosure. The system is configured to detect the contrast-enhancing agent present in the urine located in an ureter to differentiate the ureter and other surrounding tissues.

In another embodiment, a biological tissue may be imaged with a system according to the instant disclosure ex vivo. In such an application, the biological sample may be removed and analyzed outside of the surgical site. Traditional staining methods may be applied to the resected tissue to determine one or more biological characteristics of the sample. Ex vivo techniques are known in the art and would be apparent to one of skill in the art in view of this disclosure.

In another embodiment, the biological sample may be enhanced by applying a digital stain to the sample. Digital stains are applied to an image data set by using an algorithm. The use of a digital stain eliminates the need to apply a physical and/or chemical stain to the biological sample. Digital stains may be applied to any of the image data sets obtained through the systems disclosed herein. One example of the application of a digital stain to a Raman data set may be found in U.S. Patent Application Publication Number 2012/0083678, filed as application Ser. No. 13/200,779 on Sep. 30, 2011 to Drauch et al. and entitled SYSTEM AND METHOD FOR RAMAN CHEMICAL ANALYSIS OF LUNG CANCER WITH DIGITAL STAINING, assigned to ChemImage Corporation, Pittsburgh, Pa., the entirety of which is incorporated herein by reference.

Not intending to limit the disclosure in any way, the instant disclosure is directed to analyzing a ureter via an endoscope. Other medical imaging instrumentation and the detection of other types of biological samples is further contemplated by the instant disclosure and would be apparent to those of skill in the art in view of the instant disclosure.

The medical imaging instruments disclosed herein provide real-time multivariate imaging by generating a multivariate signal using one or more detectors. The detectors detect the multivariate signal to produce one or more image data sets. Provided herein are two ways to achieve this result. One such method includes illuminating a sample, collecting interacted photons that have interacted with the sample, and modulating the collected signal prior to passing the signal on to a detector. A second method includes modulating the illumination source signal prior to interaction with a sample, collecting interacted photons of the modulated signal, and detecting the interacted photons of the signal. Both processes provide a modulated signal to produce a multivariate chemical image in real-time with enhanced contrast to assist surgeons with delicate medical procedures. The embodiments contained herein can further be configured to provide real-time images displayed in stereo vision. Such a configuration would be apparent to those of skill in the art in view of this disclosure. Stereo vision further assists a surgeon by providing the depth perception needed in medical procedures employing medical imaging techniques, such as in endoscopic procedures. Systems and methods recited herein provide exemplary embodiments of the instant disclosure and are not intended to limit the disclosure to any particular embodiment.

In the following illustrated embodiments, like reference characters refer to like parts.

Modulating Collected Optical Signal

The following embodiment features modulating an optical signal after the collection of photons that have interacted with a sample.

System Having Conformal Filters in a Dual Polarization Arrangement:

Referring now to FIG. 1, a biological sample 100 may be illuminated and/or excited by an illumination source 103. In one embodiment, the illumination source 103 may comprise a quartz tungsten halogen light source. In other embodiments, the illumination source may comprise a metal halide light source, a light emitting diode (LED), a LED array having a uniform selection of emitters which emit over a constant wavelength range or a plurality of emitters which emit over a diversity of wavelength ranges, a pulsed LED, a pulsed LED array, a laser, a pulsed laser, a broadband illumination source and/or the like. The illumination source 103 generates illuminating photons that are directed from the illumination source 103 to the distal end of an endoscope 102 through a fiber optic bundle 104. The endoscope 102 is configured to direct interacted photons 101 that have interacted with the biological sample 100 to a polarizing beam splitter 107. Two independently tunable conformal filters 105a, 105b are situated along distinct orthogonal beam paths to filter orthogonal polarization components emerging from polarizing beam splitter 107. Suitable conformal filters for use in the instant disclosure may include those disclosed in U.S. Patent Application Publication Number 2013/0176568 to Priore et al., filed Jan. 4, 2013, assigned to Chemimage Corporation and entitled CONFORMAL FILTER AND METHOD OF USE THEREOF, the entirety of which is hereby incorporated by reference.

In this arrangement, the paths of the filtered beams are not parallel through the conformal filters 105a, 105b, but are directed by appropriate reflectors, i.e., mirrors, 109a, 109b to a beam combiner 111. In alternate embodiments, the beam combiner may be a polarizing cube or polarizing beam splitter. In another embodiment, the orthogonal components may comprise the same or different multi-passband wavelengths $\Sigma\lambda_1$ and $\Sigma\lambda_2$. In the exemplary embodiment, the conformal filter 105a is configured to generate a polarized multi-passband wavelengths $\Sigma\lambda_1$ and conformal filter 105b is configured to generate a polarized multi-passband wavelengths $\Sigma\lambda_2$. In the exemplary embodiment, multi-passband wavelengths $\Sigma\lambda_1$ and $\Sigma\lambda_2$ are directed to a detector 115 through a lens assembly (not shown). In another embodiment, the multi-passband wavelengths $\Sigma\lambda_1$ and $\Sigma\lambda_2$ may be combined as they are directed to the detector 115. In some embodiments, beam paths from the polarizing beam splitter 107 to the beam combiner 111 may be made symmetrical to avoid, for example, a need for infinitely-corrected optics.

The detector 115 as illustrated comprises a CCD detector. However, the present disclosure contemplates that the detector 115 may comprise other suitable detectors including, for example, a complementary metal-oxide-semiconductor, a (CMOS) detector, an indium gallium arsenide (InGaAs) detector, a platinum silicide (PtSi) detector, an indium antimonide ("InSb") detector, a mercury cadmium telluride ("HgCdTe") detector, or combinations thereof. Still referring to FIG. 1, the two conformal filters 105a and 105b may be tuned in unison to the same multi-passband wavelengths ($\Sigma\lambda_1=\Sigma\lambda_2$) using an controller 117. In another embodiment, the controller 117 may be configured to independently tune each multi-passband wavelengths $\Sigma\lambda_1$ and $\Sigma\lambda_2$ to respectively process orthogonal components of the input. Therefore, by appropriate control, the conformal filters 105a and 105b may be tuned to the same multi-passband wavelengths or to two different multi-passband wavelengths ($\Sigma\lambda_1 \neq \Sigma\lambda_2$) at the same time. The controller 117 may be programmable or software-implemented to allow a user to selectively tune each conformal filter as desired. In the embodiment of FIG. 1, a fast switching mechanism (not shown) may be provided to switch between the two views (or spectral images) corresponding to spectral data collected by the detector 117 from each of the conformal filters 105a and 105b. Alternatively, two such spectral views or images may be combined or overlaid into a single image to increase contrast or intensity, or for the purpose of comparison. The exemplary embodiment in FIG. 1 comprises a single CCD detector 115 to capture the filtered signals received from the conformal filters 105a and 105b.

Figure 1A:
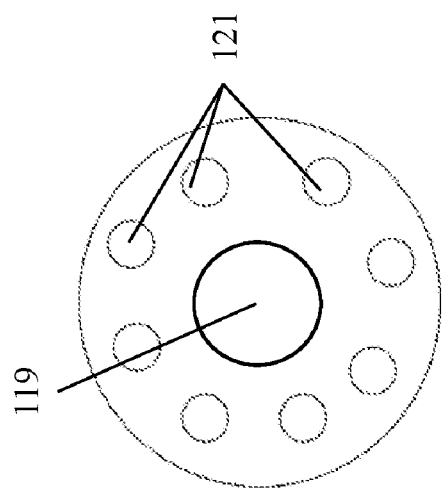
FIG. 1A is an end-on view of the endoscope according to the embodiment in FIG. 1.
Figure 1B:
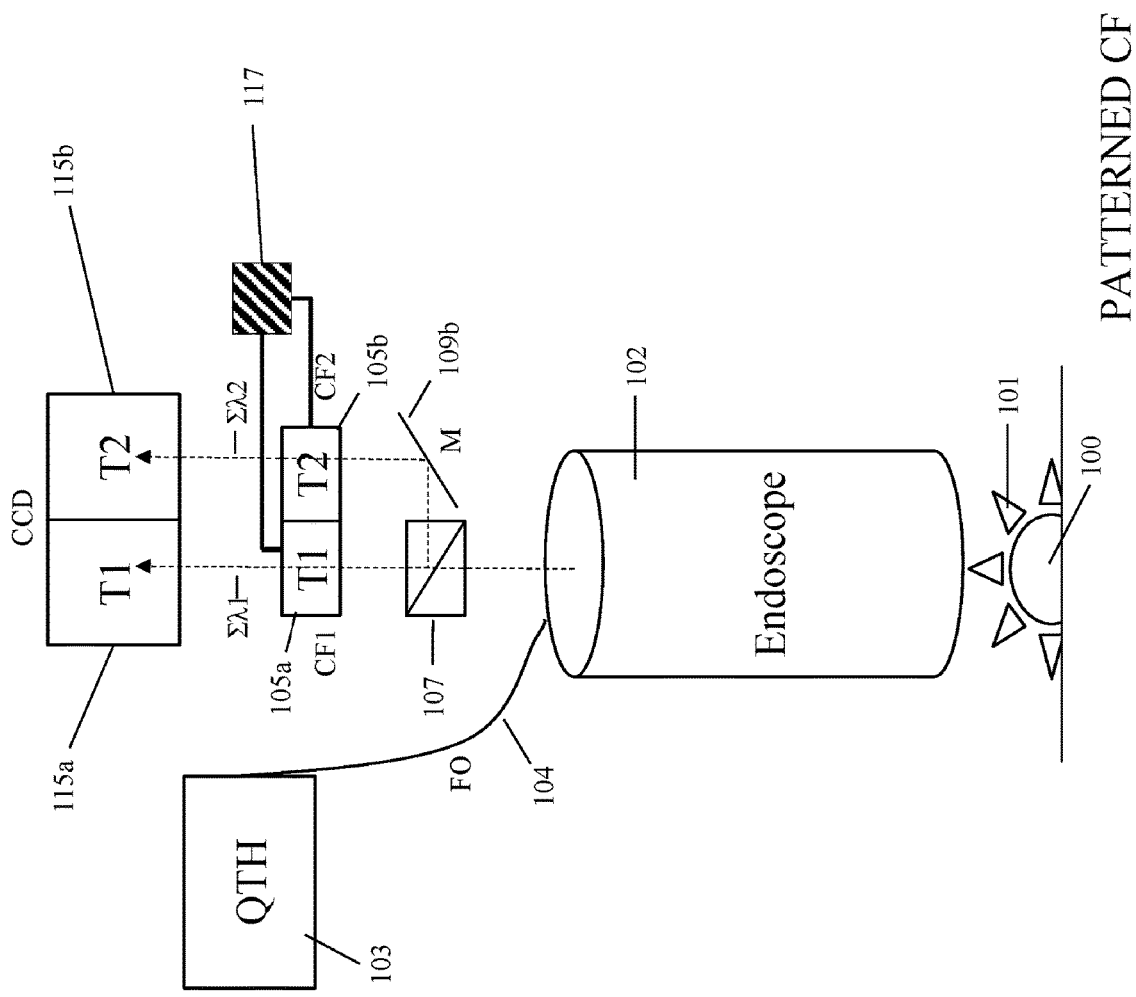
FIG. 1B illustrates a patterned conformal filter configuration with a CCD detector, according to an embodiment.

FIG. 1B illustrates an alternative embodiment of the instant disclosure. In this embodiment, the beam combiner 111 and mirror 109a may be removed and two detectors may be used. The first conformal filter 105a is configured to filter and transmit first multi-passband wavelengths corresponding to a T1 state to a first detector 115a where the first detector 115a detects the first multi-passband wavelengths and generates a first image data set (T1). In similar fashion, the second conformal filter 105b is configured to filter and transmit second multi-passband wavelengths corresponding to a T2 state to a second detector 115b where the second detector 115b detects the second multi-passband wavelengths and generate a second image data set (T2).

U.S. Patent Application Publication Number 2014/0198315 to Treado et al., filed Jan. 15, 2014 assigned to Chemimage Corporation and entitled SYSTEM AND METHOD FOR ASSESSING ANALYTES USING CONFORMAL FILTERS AND DUAL POLARIZATION discloses the use of conformal filters in a dual polarization configuration as discussed above. The reference is hereby incorporated by reference in its entirety.

FIG. 1A illustrates an end-on view of the distal end of the endoscope 102. The distal end features a lens 119 for collecting interacted photons 101 and fiber ends 121 of the fiber optic bundle 103 which illuminate the biological sample 100 to generate the interacted photons 101. The detector 115 detects the multi-passband wavelength from the conformal filters 105a and 105b and is configured to generate one or more image data sets. The image data set may comprise a T1 image corresponding to the first multi-passband wavelengths $\Sigma\lambda_1$ and a T2 image corresponding to the second multi-passband wavelengths $\Sigma\lambda_2$. In one embodiment, the image data set comprises a Raman image data set. The one or more image data sets generated by the detector 115 may be further analyzed as set forth below.

System Having MOE Filter Arrangements

Figure 2:
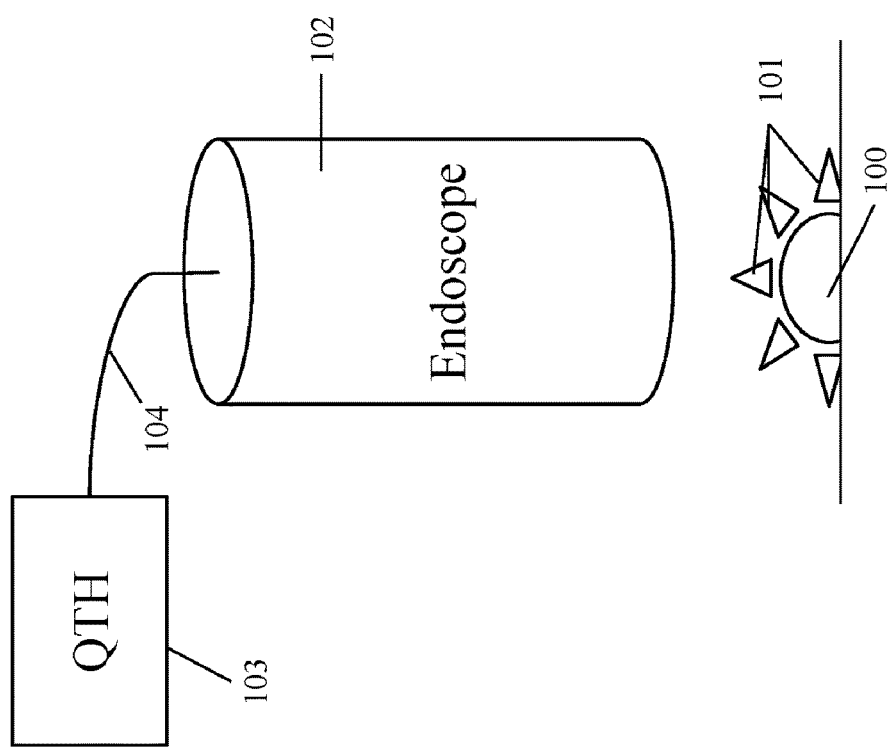
FIG. 2 illustrates an endoscope comprising an imaging system having a plurality of multivariate optical element (MOE) filters, according to an embodiment.
Figure 2A:
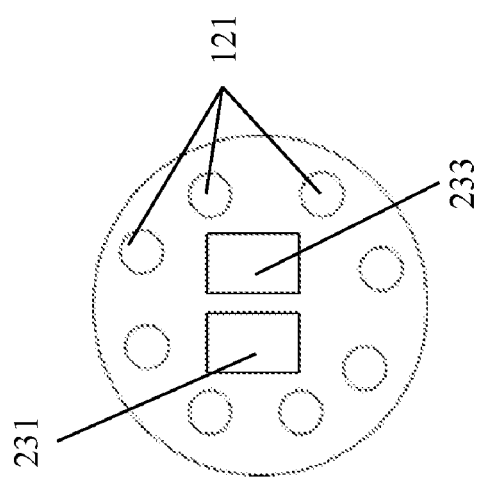
FIG. 2A is an end-on view of the endoscope according to the embodiment in FIG. 2.
Figure 2B:
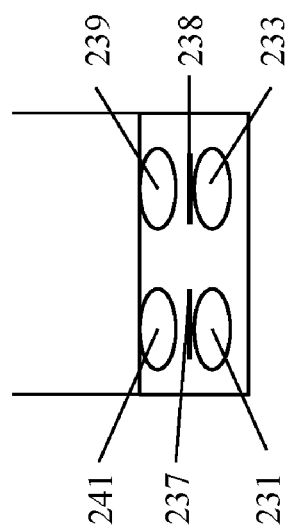
FIG. 2B is a cross-sectional view of the distal end of the endoscope according to the embodiment in FIG. 2.

FIG. 2 illustrates another embodiment featuring modulating the collected optical signal. In FIG. 2, an illumination source 103 generates illuminating photons which traverse along a fiber optic bundle 104 through an endoscope 102 and terminate at a series of fiber ends 121 on the distal end of the endoscope 102 (shown in FIG. 2A). The fiber ends 121 emit illuminating photons to illuminate a sample 100 to produce a plurality of interacted photons 101. The interacted photons are collected by a first collection optic 231 and a second collection optic 233. The first collection optic 231 collects a first portion of the interacted photons 101 and passes these photons on to a first Multivariate Optical Element "MOE" filter 237 which filters the first portion of the interacted photons 101 to generate a first portion of filtered photons. The first portion of filtered photons is detected by a first detector 241. Further, the second collection optic 233 collects a second portion of the interacted photons 101 and passes these photons on to a second MOE filter 238 to generate a second portion of filtered photons. The second portion of filtered photons is detected by a second detector 239. In one embodiment, the first detector 239 and the second detector 241 are CCD detectors. In other embodiments, the detectors 239 and 241 may comprise other suitable detectors including, for example, a complementary metal-oxide-semiconductor, a (CMOS) detector, an indium gallium arsenide (InGaAs) detector, a platinum silicide (PtSi) detector, an indium antimonide ("InSb") detector, a mercury cadmium telluride ("HgCdTe") detector, or combinations thereof.

In one embodiment, the first MOE filter 237 may be configured to generate a first filtered passband. In one embodiment, the first MOE filter 237 is configured to generate a first filtered passband consistent with a randomized target or background. In one embodiment, the second MOE filter 238 may be configured to generate a second filtered passband consistent with the target or sample 100. In embodiments where the first MOE filter 231 is configured to generate a first filtered passband corresponding to a randomized target or background, the second MOE filter 238 may be configured to generate a second filtered passband corresponding to a target or sample. This type of embodiment permits discrimination of both a target and a background.

MOEs are typically known in the art. An MOE features wide-band, optical interference filters encoded with an application-specific regression (or pattern) specific to a target. MOEs provide multivariate optical computing by performing the optical computation based on the pattern of the filter. In other words, MOEs are uniquely tuned to the pattern that needs to be measured using multivariate analysis on the filter as opposed to capturing multiple measurements at different wavelengths to estimate the full spectrum of a target and processing this information by applying multivariate statistics to the spectrum. Thus, MOEs increase throughput and efficiency over conventional filters, which can increase the speed of analysis. Suitable MOEs would be apparent to those of skill in the art in view of this disclosure.

The first detector 241 is configured to detect the first filtered passband from the first MOE filter 237 to generate a first image data set (T1), and the second detector 239 is configured to detect the second filtered passband from the second MOE filter 238 to generate a second image data set (T2). The first image data set and the second image data set may be further analyzed, as set forth below.

Modulating Illumination Source Signal

The following embodiments feature modulating the illumination source signal prior to interaction with a sample.

System Having a Conformal Filter Arrangement

Figure 3:
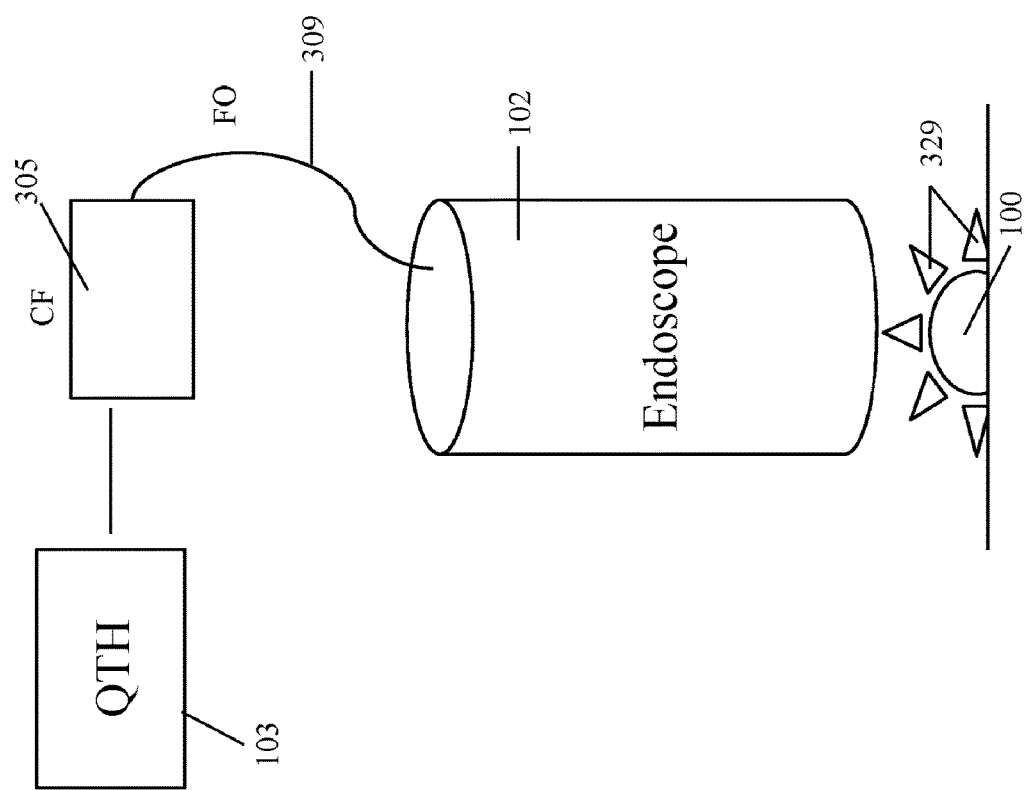
FIG. 3 illustrates an endoscope comprising an imaging system having a conformal filter, according to an embodiment.
Figure 3A:
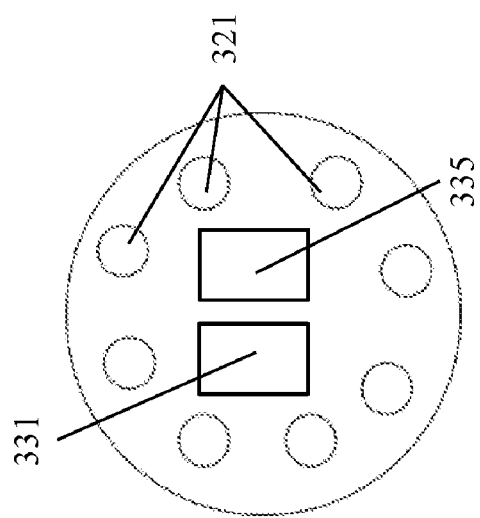
FIG. 3A is an end-on view of the endoscope according to the embodiment in FIG. 3.

FIG. 3 illustrates an illumination source 103 configured to generate illuminating photons which are transmitted through a filter 305. In one embodiment, the filter 305 comprises a conformal filter, as disclosed herein. In another embodiment, the filter 305 may comprise other filters, such as a liquid crystal tunable filter ("LCTF"), or filters as would be apparent to those of skill in the art in view of this disclosure. In one embodiment, the filter 305 may include a multi-conjugate filter. The filter 305 is controlled by a controller (not shown) that is configured to switch the filter configuration to pass first multi-passband wavelengths ($\Sigma\lambda_1$) and subsequently be switched to configure the filter to pass a second multi-passband wavelengths ($\Sigma\lambda_2$). In one embodiment, the rate at which the controller switches between the two states is on a millisecond order of magnitude. The filter 305 transmits each multi-passband wavelengths, $\Sigma\lambda_1$ and $\Sigma\lambda_2$, through a fiber optic bundle 309 to the distal end of an endoscope 102 where each multi-passband wavelengths exits the distal end of the endoscope 102 via fiber ends 321, as shown in FIG. 3A, to illuminate the sample 100 and produce interacted photons 329. The interacted photons 329 are collected by a first detector 331 and a second detector 335 located on the distal end of the endoscope 102. The detectors 331 and 335 of the illustrated embodiment comprise CCD detectors. However, other detectors, such as disclosed herein, may be employed. The first detector 331 may be configured to detect substantially only the first multi-passband wavelengths. In one embodiment, the first detector 331 may be timed, i.e., turned off and on, to detect the first multi-passband wavelengths concurrent with the filter 305 transmitting the first multi-passband wavelengths. Likewise, the second detector 335 may be configured to detect substantially only the second multi-passband wavelengths. In one embodiment, the second detector 335 may be timed, i.e., turned off and on, to detect the second multi-passband wavelengths concurrent with the filter 305 transmitting the second multi-passband wavelengths. In another embodiment, the timing sequence of the modulation between the first multi-passband wavelengths and the second multi-passband wavelengths and the detection of the first multi-passband wavelengths and the second multi-passband wavelengths with the corresponding detector may be controlled by the controller (not shown). The first detector 231 detects the first multi-passband wavelengths and generates a first image data set (T1) and the second detector detects the second multi-passband wavelengths and generates a second image data set (T2). In one embodiment, the first image data set and the second image data set may be further analyzed as set forth below.

System Having a Conformal Filters in Dual Polarization Arrangement

Figure 4:
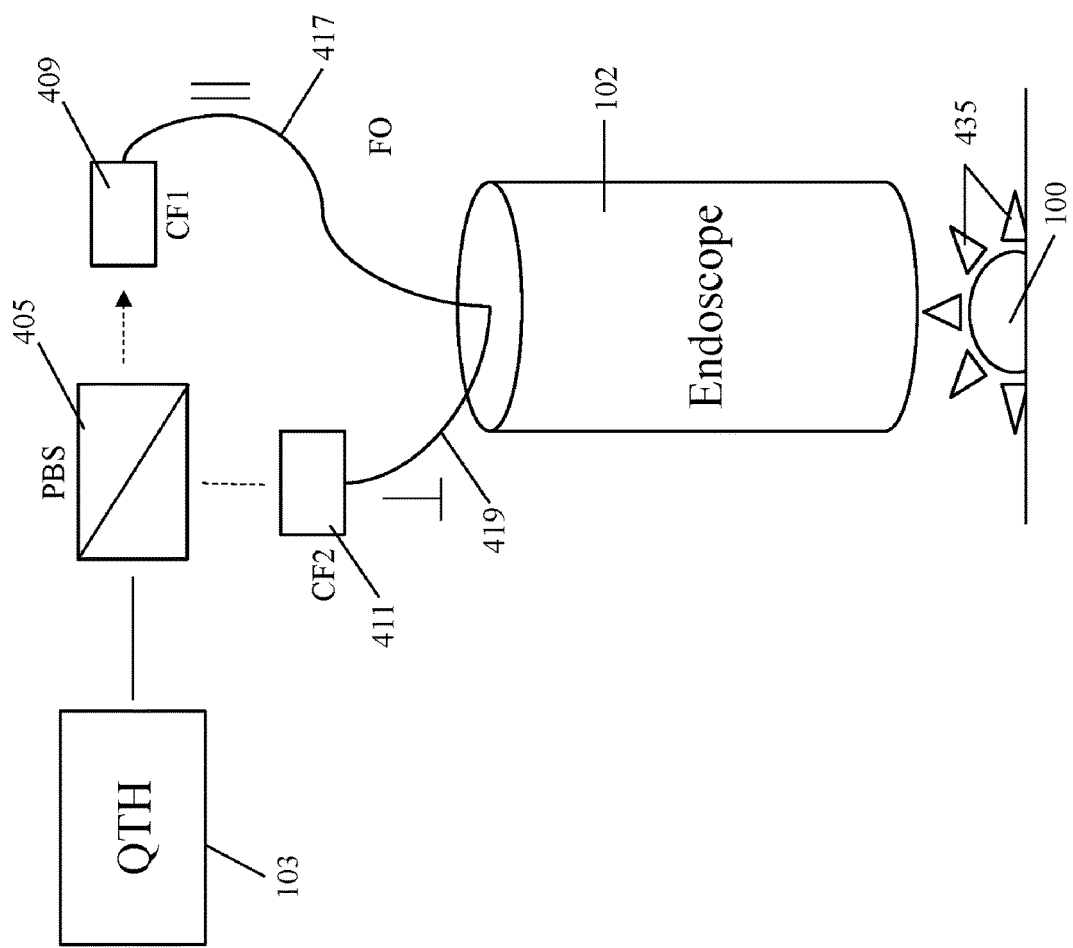
FIG. 4 illustrates an endoscope comprising an imaging system having a plurality of conformal filters in a dual polarization configuration for source illumination modulation, according to an embodiment.

FIG. 4 illustrates another embodiment of illumination source modulation. In this embodiment, an illumination source 103 generates an optical signal that is transmitted through a polarizing beam splitter 405 which splits the optical signal into a first polarization signal and a second polarization signal. The first polarization signal is transmitted to a first filter 409, and the second polarization signal is transmitted to a second filter 411. In one embodiment, the first filter 409 and the second filter 411 each comprise conformal filter, as described herein. In another embodiment, the first filter 409 and second filter 411 comprise an LCTF. In one embodiment, the first filter 409 and the second filter 411 each may comprise a multi-conjugate filter. The first filter 409 is configured to filter the first polarization signal and transmit a first multi-passband wavelengths ($\Sigma\lambda_1$), and the second filter 411 is configured to filter the second polarization signal and transmit second multi-passband wavelengths ($\Sigma\lambda_2$). The first multi-passband wavelengths and the second multi-passband wavelengths are transmitted from their respective filters 409, 411 to the distal end of an endoscope 102 via a first fiber optic bundle 417 and second fiber optic bundle 419. In one embodiment, the first fiber optic bundle 417 and the second fiber optic bundle 419 comprise a polarization-maintaining fiber optic bundle.

Figure 4A:
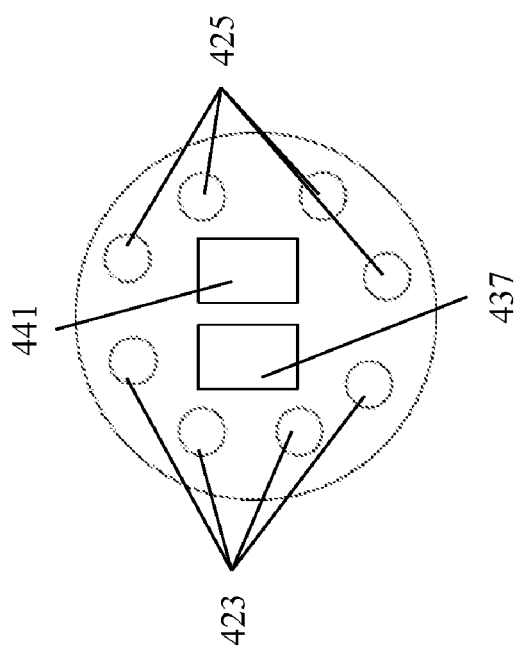
FIG. 4A is an end-on view of the endoscope according to the embodiment in FIG. 4.
Figure 4B:
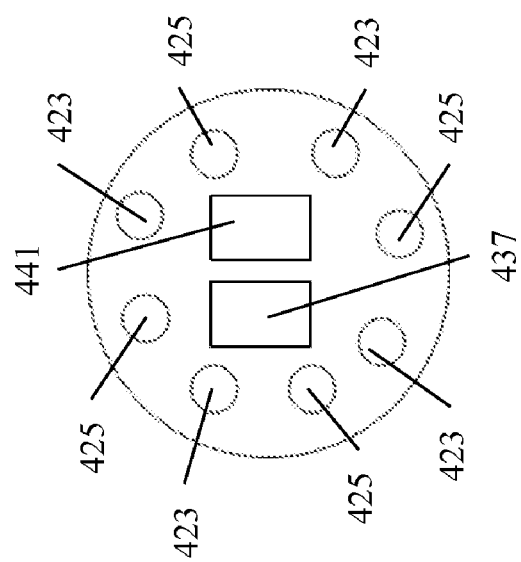
FIG. 4B is an end-on view of an alternate embodiment of the endoscope according to the embodiment in FIG. 4.

FIG. 4A and FIG. 4B illustrate different embodiments of the distal end of the endoscope 102. The first fiber bundle 417 and a the second fiber bundle 419 traverse through the endoscope 102 to the distal end. The first fiber bundle 417 terminates at first fiber ends 423 and the second fiber bundle 417 terminates at second fiber ends 425. FIG. 4A illustrates one exemplary arrangement of the first fiber ends 423 with respect to the second fiber ends 425. In this embodiment, the first fiber ends 423 are distributed together on one side of the distal end of the endoscope 102 and the second fiber ends 425 are distributed together on the other side of the distal end of the endoscope 102. In FIG. 4B, another embodiment is shown where the first fiber ends 423 and the second fiber ends 425 alternate around the distal end of the endoscope 102. Suitable arrangements of the fiber ends would be apparent to those of skill in the art in view of this disclosure. The sample 100 is illuminated from the multi-first passband wavelengths and the second multi-passband wavelengths emitting from the first fiber ends 423 and the second fiber ends 425, respectively, to generate interacted photons 435. The interacted photons 435 are detected by a first detector 437 and a second detector 441 disposed on the distal end of the endoscope 102. In the illustrated embodiment, the first detector 437 and the second detector 441 are CCD detectors. However, other suitable detectors, such as those disclosed herein, may be employed and such detectors would be apparent to one of skill in the art in view of this disclosure. In one embodiment, the first fiber bundle 417 and the second fiber bundle 419 comprise polarization maintaining fiber bundles. In such an embodiment, polarizers (not shown) may be disposed in front of the detectors 437 and 441, which are arranged for stereovision, and configured to differentiate between a T1 state and a T2 state on the basis of polarization. In one embodiment, the first detector 437 is configured to detect substantially only interacted photons generated from the first multi-passband wavelengths, and the second detector 441 is configured to detect substantially only interacted photons generated from the second multi-passband wavelengths. As such, the location of the first fiber ends 423 and second fiber ends 425 with respect to the first detector 437 and the second detector 441 can be arranged to optimize the detection of the interacted photons corresponding to the first multi-passband wavelengths by the first detector 437 and the interacted photons corresponding to second multi-passband wavelengths by the second detector 441. Once the first detector 437 and the second detector 441 detect the interacted photons 435, the first detector 437 is configured to generate a first image data set (T1), and the second detector 441 is configured to generate a second image data set (T2). In one embodiment, the first image data set and the second image data set may be further analyzed.

System Having an Acousto-Optic Filter Arrangement

Figure 5:
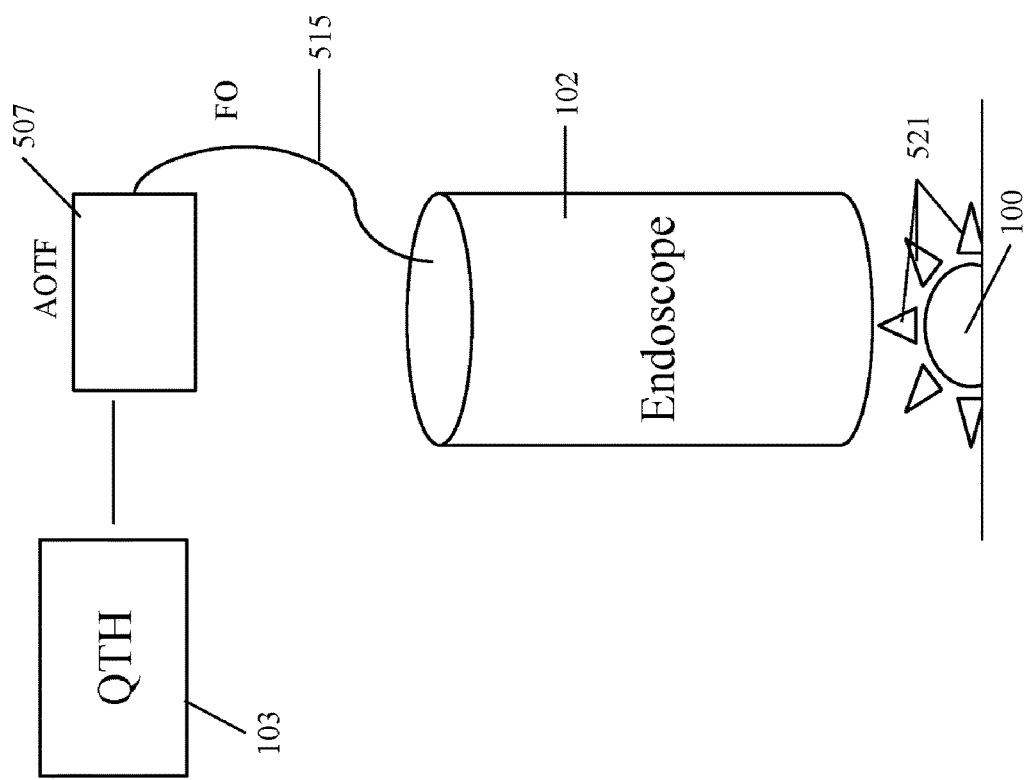
FIG. 5 illustrates an endoscope comprising an imaging system having an acousto-optic filter, according to an embodiment.

FIG. 5 illustrates an embodiment of the instant disclosure employing an acousto-optic tunable filter (AOTF). This embodiment features an illumination source 103 to generate illuminating photons for illuminating a sample 100. A filter 507 is configured to filter photons emitted from the illumination source 103. In one embodiment, the filter 507 comprises an AOTF in which the AOTF transmits a single passband wavelength. To achieve a >10 fps sampling rate, the AOTF is rapidly switched between target vs background passband wavelengths. In another embodiment, the filter comprises a conformal filter based on AOTF technology in which the AOTF transmits multi-passband wavelengths simultaneously. To switch between T1 and T2 states, the conformal filter AOTF is switched in series with microsecond switching speeds. In other embodiments, multiple conformal AOTFs may be employed in which the T1 and T2 states are selected simultaneously. In embodiments employing multiple acousto-optic filters, each filter may be tuned to various wavelengths where each filter transmits different multi-passband wavelengths simultaneously.

Acousto-optic filters are known in the art and, generally, operate by passing a beam of source light through a substrate, typically quartz. The substrate is vibrated by a piezoelectric transducer modulator. An RF frequency is applied to the modulator, causing the substrate to vibrate. Source light or radiation is passed through the vibrating substrate, which causes the source light passing through the substrate to diffract, thus creating a filter gradient for the source light. The source light emitted from the acousto-optic filter can be filtered to a desired passband wavelength by the RF frequency applied to the piezoelectric transducer. Details on the operation of an acousto-optic filter are described in more detail in Turner, John F. and Treado, Patrick J. "Near-Infrared Acousto-Optic Tunable Filter Hadamard Transform Spectroscopy" *Applied Spectroscopy*, 50.2 (1996), 277-284, which is hereby incorporated by reference in its entirety.

Figure 5A:
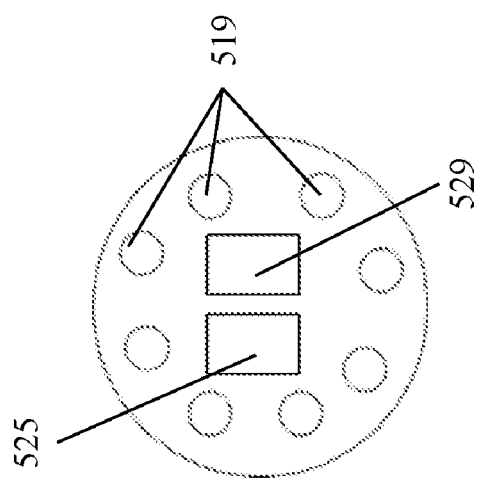
FIG. 5A is an end-on view of the endoscope according the embodiment in FIG. 5.

The passband wavelength transmitted from the filter 507 is transmitted to the distal end of an endoscope 102 through a fiber optic bundle 515. FIG. 5A illustrates the distal end of the endoscope 102 and features a plurality of fiber ends 519 from the fiber optic bundle 515. The fiber ends 519 transmit the passband wavelength from the filter 507 to illuminate the sample 100 to produce interacted photons 521 which are detected by a first detector 525 and a second detector 529 located on the distal end of the endoscope 102. In one embodiment, only one detector is used, i.e., the first detector 525, to detect a plurality of the interacted photons 521. In another embodiment, the interacted photons 521 are detected by both detectors 525 and 529. In another embodiment, a plurality of acousto-optic filters are employed and generate a first passband wavelength and a second passband wavelength. The first detector 525 may be configured to detect the first passband wavelength and generate a first image data set (T1), and the second detector 529 may be configured to detect the second passband wavelength and generate a second image data set (T2). In one embodiment, the first image data set and the second image data set may be further analyzed as set forth below.

System Having an MOE Filter Wheel Arrangement

Figure 6:
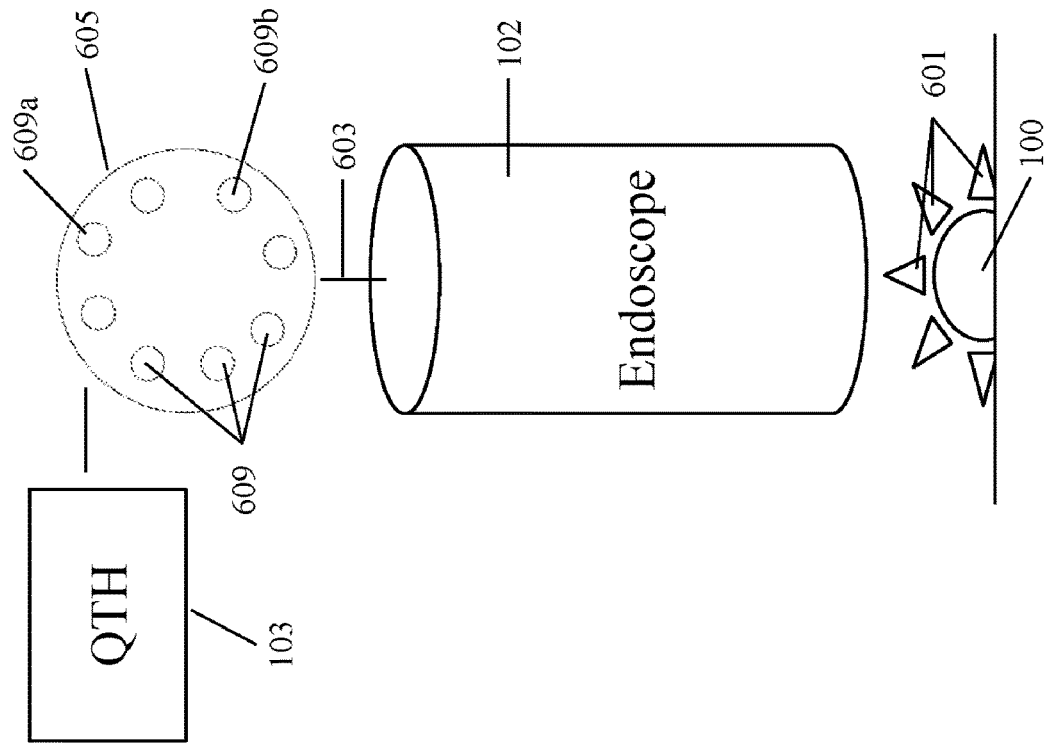
FIG. 6 illustrates an endoscope comprising an imaging system having a MOE filter wheel, according to an embodiment.

FIG. 6 illustrates another embodiment according to the instant disclosure. An illumination source 103 generates illuminating photons which are transmitted to a filter wheel 605 where the illuminating photons are filtered to generate filtered photons. The filter wheel 605 comprises a plurality of filter elements 609. In one embodiment, each filter element 605 comprises an MOE. Suitable MOEs for use in the instant disclosure are known in the art and described herein. Each filter element 609 may be different and each filter element may be configured to filter and transmit a different passband wavelength. For example, filter element 609a may be configured to transmit a wavelength corresponding to a background, such as a specific type of tissue or anatomical structure, and filter element 609b may be configured to transmit a passband wavelength corresponding to an anomaly in a tissue sample, such as a cancerous tumor on the tissue. In this type of embodiment, the filter wheel 605 can be rotated during a surgical procedure to assist a surgeon in distinguishing normal tissue from cancerous tissue. In another embodiment, the filter elements 609 are configured to detect a plurality of different samples. In one embodiment, the filter elements 609 are configured to discriminate background tissue from an anatomical structure such as a ureter.

Figure 6A:
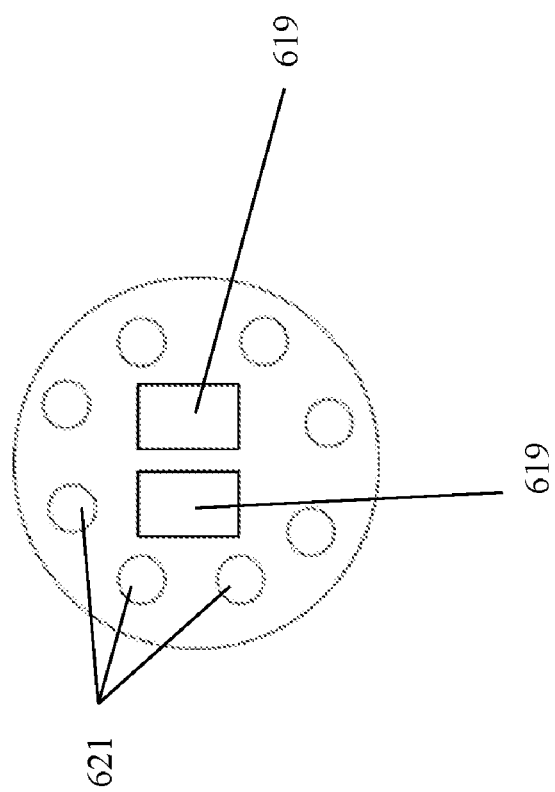
FIG. 6A is an end-on view of the endoscope according to the embodiment in FIG. 6.

The filtered photons are transmitted via a fiber optic bundle 603 to the distal end of the endoscope 102 and exit the distal end of the endoscope through a plurality of fiber ends 621 as shown in FIG. 6A. The filtered photons illuminate the sample 100 and generate a plurality of interacted photons 601. The interacted photons 601 are detected by a one or more detectors 619, and the one or more detectors 619 is configured to generate an image data set (T1). In one embodiment, the image data set may be further analyzed, as set forth below.

System Having a Patterned Etalon Filter Arrangement

Figure 7:
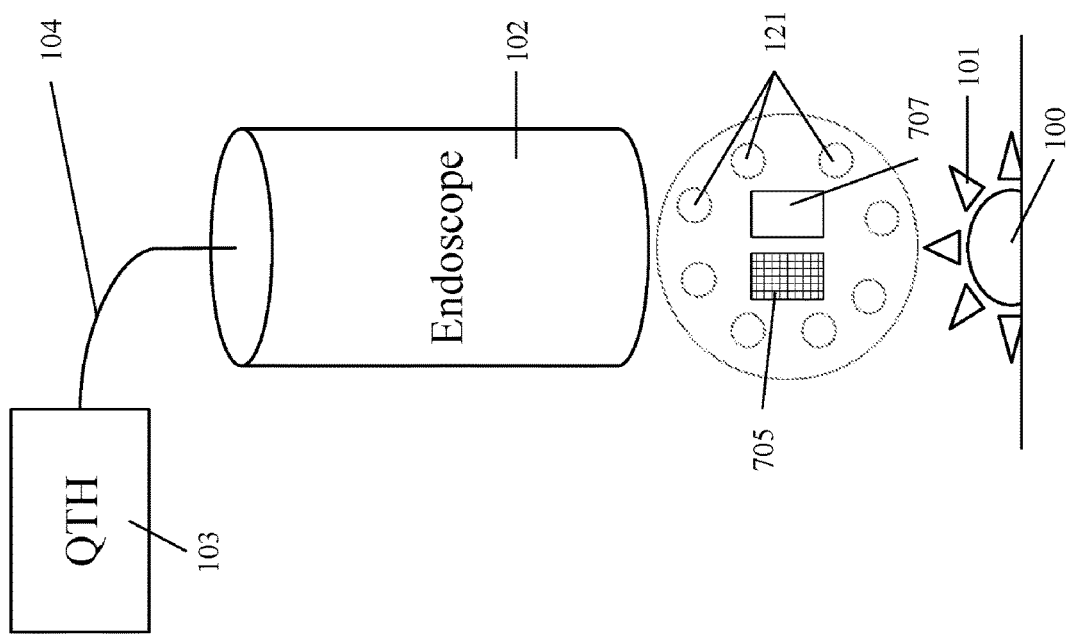
FIG. 7 illustrates an endoscope comprising an imaging system having a patterned etalon filter arrangements, according to an embodiment.

FIG. 7 illustrates another embodiment of the instant disclosure. Illumination source 103 generates illuminating photons which are transmitted through a fiber optic bundle 104 to the distal end of the endoscope 102 to fiber ends 121. Illuminating photons exit the fiber ends 121 and illuminate the sample 100 and generate interacted photons 101 from the sample 100. The interacted photons 101 are detected by a first detector 705 and a second detector 707 disposed on the distal end of the endoscope 102. In one embodiment, the first detector 705 and the second detector 707 comprise hyperspectral cameras. In one embodiment, the detectors 705 and 707 comprise a Fabry-Perot interferometric (patterned etalon) filter configuration disposed on each pixel of the detector. Suitable examples of patterned etalon filter arrangements and associated detectors are available from Ximea Corporation. The filter on each pixel is configured to transmit one or more passband wavelengths for each pixel. In one embodiment, the first detector 705 comprises a patterned etalon filter arrangement in a mosaic snapshot arrangement. A mosaic snapshot can be acquired over 1088× 2048 pixels. In one embodiment, the mosaic snapshot comprises a 4×4 mosaic having 16 wavelength bands. In another embodiment, the mosaic snapshot comprises a snapshot of the sample from 465-630 nm at 11 nm intervals. In another embodiment, the mosaic snapshot may comprise a 5×5 mosaic having 25 bands over a wavelength range from about 600 to 1,000 nm. The mosaic snapshot may include a spatial resolution per band of about 512×272 with up to 2 megapixels with interpolation and may collect up to 170 data-cubes/sec.

In another embodiment, the first detector 705 and the second detector 707 may comprise a patterned etalon filter arrangement for obtaining a snapshot tiled configuration. In one embodiment, the snapshot tiled configuration transmits a passband wavelength at each pixel. The patterned etalon snapshot tiled filter configuration can acquire up to 1088× 2048 pixels. In one embodiment, the tiled snapshot has a spectral resolution of up to 32 bands and can detect wavelengths ranging from 600-1,000 nm over 12 incremental steps. In another embodiment, the spatial resolution per band is about 256×256. In another embodiment, the tiled snapshot may detect up to 170 data-cubes/sec. The patterned etalon filter arrangement may also be customized to generate a predetermined response based on the sample to be analyzed and the result desired. Such customization would be apparent to one of skill in the art in view of this disclosure.

In one embodiment, the first detector 705 and the second detector 707 comprise IMEC mosaic filter arrangements. In such an embodiment, the patterned etalon mosaic filter arrangements of the first detector 705 and the second detector 707 are configured to transmit one or more different wavelength bands at each pixel. In another embodiment, the first detector 705 and the second detector 707 comprise patterned etalon tiled filter arrangements. In such an embodiment, the patterned etalon tiled filter arrangements of the first detector 705 and the second detector 707 are configured to detect a different wavelength band at each pixel. In another embodiment, the second detector is eliminated and the embodiment employs the first detector 705 having either a snapshot mosaic patterned etalon filter arrangement or a snapshot tiled patterned etalon filter arrangement.

The detectors 705 and 707 are configured to generate one or more image data sets for each passband wavelength transmitted from the filter arrangements. In one embodiment, the detectors 705 and 707 are configured to generate a first image data set (T1) and a second image data set (T2). In one embodiment, the image data sets may be further analyzed, as set forth below.

In yet another embodiment, an illumination source may be configured to generate illuminating photons at specific wavelengths. For example, the illumination source may comprise a plurality of LEDs where a first portion of the LEDs are configured to generate a first wavelength and a second portion of the LEDs are configured to generate a second wavelength for illuminating a sample. In such an embodiment, a first detector may be configured to detect interacted photons from the first wavelength and generate a first image data set (T1), and a second detector may be configured to detect interacted photons from the second wavelength and generate a second image data set (T2). Other illumination sources or arrangements may be employed which are capable of producing illuminating photons at a plurality of wavelengths. In one embodiment, the illumination source comprises a modulating laser which is capable of generating multiple wavelengths.

The image data sets described herein may comprise one or more of an ultraviolet (UV) image data set, fluorescence image data set, a visible (VIS) image data set, a Raman image data set, a near-infrared (NIR) image data set, a short-wave infrared (SWIR) data set, a mid-infrared (MIR) data set, and a long-wave infrared (LWIR) data set. In another embodiment, the image data set comprises a hyperspectral image data set. The image data sets of the instant disclosure may further be analyzed. In one embodiment, the systems disclosed herein may include a fiber array spectral translator (FAST). Suitable FAST devices are disclosed in U.S. Pat. No. 8,098,373 to Nelson et al., entitled SPATIALLY AND SPECTRALLY PARALLELIZED FIBER ARRAY SPECTRAL TRANSLATOR SYSTEM AND METHOD OF USE, filed Apr. 13, 2010 and assigned to Chemimage Corporation, the disclosure of which is incorporated by reference in its entirety.

In one embodiment, the systems disclosed herein may comprise a processor and a non-transitory processor-readable storage medium in operable communication with the processor. The storage medium may contain one or more programming instructions that, when executed, cause the processor to analyze the image data sets. In one embodiment, the analysis may comprise applying an optical computation to the data set. In another embodiment, the optical computation may comprise one or more of T1, and (T1-T2)/(T1+T2). Other optical computations known in the art may be applied. In one embodiment, the analysis may comprise applying one or more chemometric techniques to the image data sets. The chemometric analysis may comprise one or more of a multivariate curve resolution analysis, a principle component analysis (PCA), a partial least squares discriminant analysis (PLSDA), a k means clustering analysis, a band t entropy analysis, an adaptive subspace detector analysis, a cosine correlation analysis, a Euclidian distance analysis, a partial least squares regression analysis, a spectral mixture resolution analysis, a spectral angle mapper metric analysis, a spectral information divergence metric analysis, a Mahalanobis distance metric analysis, and spectral unmixing analysis. In some embodiments, the processor may be configured to control operation of the system. For example, in embodiments where a tunable filter is employed, the process may be configured to cause the a controller to apply voltages to the tunable filter to obtain the desired passband transmission. Further, the processor may be configured to control timing of an illumination source and detectors so that the correct detector is in operation for the specific illumination. Other processor configurations are contemplated and would be apparent to one of skill in the art in view of this disclosure.

The systems according to the instant disclosure may further include a display. In some embodiments, the display may include one or more results from one or more of the detectors. In another embodiment, the display may include one or more results from the analysis of the processor. In one embodiment, the display may include one or more results from one or more of the detectors and one or more results from the analysis of the processor.

What is claimed is:

1. An intraoperative device comprising:
an imaging system including:
an illumination source configured to generate a plurality of illuminating photons to illuminate a biological sample and produce a plurality of interacted photons;
an optical signal modulator configured to receive the plurality of illuminating photons or the plurality of interacted photons and generate a first optical component having a first set of multi-passband wavelengths and a second optical component having a second set of multi-passband wavelengths, the optical signal modulator comprising two or more of conformal filters, multivariate optical element (MOE) filters, patterned etalon filters, acousto-optical tunable filters (AOTF), liquid crystal tunable filters (LCTF), multi-conjugate filters, and combinations thereof to generate the first optical component and the second optical component;
a single detector configured to receive the first optical component and the second optical component from the optical signal modulator and generate a first image data set (T1) corresponding to the first optical component and a second image data set (T2) corresponding to the second optical component; and
a processor configured to analyze the first image data set (T1) and the second image data set (T2).

2. The device of claim 1, wherein the illumination source includes one or more of a halogen light source, a metal halide light source, a light emitting diode (LED), an LED array, a pulsed LED, a pulsed LED array, a laser, and a pulsed laser.

3. The device of claim 1, wherein the detector comprises one or more of a CCD detector, a complementary metal-oxide-semiconductor (CMOS) detector, an indium gallium arsenide (InGaAs) detector, a platinum silicide (PtSi) detector, an indium antimonide (InSb) detector, and a mercury cadmium telluride (HgCdTe) detector.

4. The device of claim 1, wherein the processor is configured to apply an optical computation to one or more of the first image data set (T1) and the second image data set (T2).

5. The device of claim 1, wherein the processor is further configured to apply a digital stain to at least one of the first image data set (T1) or the second image data set (T2).

6. The device of claim 1, wherein the processor is configured to analyze the first image data set (T1) and the second image data set (T2) to differentiate structures of the biological sample.

7. The device of claim 6, wherein the structures include a ureter and surrounding tissue.

8. The device of claim 1, wherein the processor is configured to analyze the first image data set (T1) and the second image data set (T2) by applying one or more chemometric techniques selected from a group consisting of a multivariate curve resolution analysis, a principle component analysis (PCA), a partial least squares discriminant analysis (PLSDA), a k means clustering analysis, a band t entropy analysis, an adaptive subspace detector analysis, a cosine correlation analysis, a Euclidian distance analysis, a partial least squares regression analysis, a spectral mixture resolution analysis, a spectral angle mapper metric analysis, a spectral information divergence metric analysis, a Mahalanobis distance metric analysis, and a spectral unmixing analysis.

9. The device of claim 1, wherein at least one of the first image data set (T1) or the second image data set (T2) includes a hyperspectral image.

10. The device of claim 1, wherein the optical signal modulator comprises a patterned etalon filter arrangement configured to receive the plurality of interacted photons.

11. The device of claim 1, wherein the optical signal modulator is configured to modulate the plurality of illuminating photons.

12. The device of claim 11, wherein the optical signal modulator comprises two or more conformal filters in a dual polarization arrangement and a plurality of multivariate optical elements.

13. The device of claim 1, wherein the optical signal modulator is configured to modulate the plurality of interacted photons.

14. An endoscopic instrument comprising:
a tubular body having a lumen therethrough, the tubular body having a proximal end and an operable end;
an illumination source optically connected to the operable end and configured to illuminate a biological sample and generate a plurality of interacted photons;
a collection optic disposed on the operable end;
an optical signal modulator optically connected to the collection optic and configured to receive the plurality of interacted photons and separate the plurality of interacted photons into a first optical component having a first set of multi-passband wavelengths and a second optical component having a second set of multi-passband wavelengths, the optical signal modulator comprising two or more of conformal filters, multivariate optical element (MOE) filters, patterned etalon filters, acousto-optical tunable filters (AOTF), liquid crystal tunable filters (LCTF), multi-conjugate filters, and combinations thereof to separate the plurality of interacted photons into the first optical component and the second optical component;
a first detector and a second detector configured to detect the first optical component and the second optical component, respectively, and generate a first image data set (T1) corresponding to the first optical component and a second image data set (T2) corresponding to the second optical component; and
a processor configured to analyze the first image data set (T1) and the second image data set (T2).

15. The instrument of claim 14, wherein the illumination source includes one or more of a halogen light source, a metal halide light source, a light emitting diode (LED), an LED array, a pulsed LED, a pulsed LED array, a laser, and a pulsed laser.

16. The instrument of claim 14, wherein the optical signal modulator comprises two or more conformal filters in dual polarization arrangement and a plurality of multivariate optical elements.

17. The instrument of claim 14, wherein the at least one detector comprises one or more of a CCD detector, a complementary metal-oxide-semiconductor (CMOS) detector, an indium gallium arsenide (InGaAs) detector, a platinum silicide (PtSi) detector, an indium antimonide (InSb) detector, a mercury cadmium telluride (HgCdTe) detector.

18. The instrument of claim 14, wherein the processor is configured to apply an optical computation to one or more of the first image data set (T1) and the second image data set (T2).

19. The instrument of claim 14, wherein the processor is further configured to apply a digital stain to at least one of the first image data set (T1) or the second image data set (T2).

20. The instrument of claim 14, wherein the processor is configured to analyze the first image data set (T1) and the second image data set (T2) to differentiate structures of the biological sample.

21. The device of claim 14, wherein the structures include a ureter and surrounding tissue.

22. The instrument of claim 14, wherein the processor is configured to analyze the first image data set (T1) and the second image data set (T2) by applying one or more chemometric techniques selected from a group consisting of a multivariate curve resolution analysis, a principle component analysis (PCA), a partial least squares discriminant analysis (PLSDA), a k means clustering analysis, a band t entropy analysis, an adaptive subspace detector analysis, a cosine correlation analysis, a Euclidian distance analysis, a partial least squares regression analysis, a spectral mixture resolution analysis, a spectral angle mapper metric analysis, a spectral information divergence metric analysis, a Mahalanobis distance metric analysis, and a spectral unmixing analysis.

23. The instrument of claim 14, wherein at least one of the first image data set (T1) or the second image data set (T2) includes a hyperspectral image.

24. The instrument of claim 14, wherein the optical signal modulator comprises a patterned etalon filter arrangement.

25. An endoscopic instrument comprising:
a tubular body having a lumen therethrough, the tubular body having a proximal end and an operable end;
an illumination source configured to generate a plurality of illuminating photons;
an optical signal modulator configured to receive the plurality of illuminating photons and separate the plurality of illuminating photons into a first optical component having a first set of multi-passband wavelengths and a second optical component having a second set of multi-passband wavelengths, the optical signal modulator comprising two or more of conformal filters, multivariate optical element (MOE) filters, patterned etalon filters, acousto-optical tunable filters (AOTF), liquid crystal tunable filters (LCTF), multi-conjugate filters, and combinations thereof to separate the plurality of illuminating photons into the first optical component and the second optical component;
a fiber optic configured to transmit the first optical component and the second optical component through the lumen to the operable end to illuminate a biological sample;
a collection optic disposed on the operable end;
a first detector and a second detector located on the operable end of tubular body and configured to detect one or more of the first optical component and the second optical component, respectively, and generate a first image data set (T1) corresponding to the first optical component and a second image data set (T2) corresponding to the second optical component; and a processor configured to analyze the first image data set (T1) and the second image data set (T2).

26. The instrument of claim 25, wherein the illumination source includes one or more of a halogen light source, a metal halide light source, a light emitting diode (LED), an LED array, a pulsed LED, a pulsed LED array, a laser, and a pulsed laser.

27. The instrument of claim 25, wherein the optical signal modulator comprises one or more of a plurality of conformal filters in dual polarization arrangement and a plurality of multivariate optical elements.

28. The instrument of claim 25, wherein the at least one detector comprises one or more of a CCD detector, a complementary metal-oxide-semiconductor (CMOS) detector, an indium gallium arsenide (InGaAs) detector, a platinum silicide (PtSi) detector, an indium antimonide (InSb) detector, a mercury cadmium telluride (HgCdTe) detector.

29. The device of claim 25, wherein the processor is configured to apply an optical computation to one or more of the first image data set (T1) and the second image data set (T2).

30. The device of claim 25, wherein the processor is further configured to apply a digital stain to at least one of the first image data set (T1) or the second image data set (T2).

31. The instrument of claim 25, wherein the processor is configured to analyze the first image data set (T1) and the second image data set (T2) to differentiate structures of the biological sample.

32. The instrument of claim 31, wherein the structures include a ureter and surrounding tissue.

33. The instrument of claim 25, wherein the processor is configured to analyze the first image data set (T1) and the second image data set (T2) by applying one or more chemometric techniques selected from a group consisting of a multivariate curve resolution analysis, a principle component analysis (PCA), a partial least squares discriminant analysis (PLSDA), a k means clustering analysis, a band t entropy analysis, an adaptive subspace detector analysis, a cosine correlation analysis, a Euclidian distance analysis, a partial least squares regression analysis, a spectral mixture resolution analysis, a spectral angle mapper metric analysis, a spectral information divergence metric analysis, a Mahalanobis distance metric analysis, and a spectral unmixing analysis.

34. The instrument of claim 25, wherein at least one of the first image data set (T1) or the second image data set (T2) includes a hyperspectral image.

35. A method of differentiating anatomical structures in a biological sample, comprising:

illuminating the biological sample with a plurality of illuminating photons to generate a plurality of interacted photons;

modulating one or more of the plurality of illuminating photons or the plurality of interacted photons into a first optical component having a first set of multi-passband wavelengths and a second optical component having a second set of multi-passband wavelengths, the optical signal modulator comprising two or more of conformal filters, multivariate optical element (MOE) filters, patterned etalon filters, acousto-optical tunable filters (AOTF), liquid crystal tunable filters (LCTF), multi-conjugate filters, and combinations thereof to generate the first optical component and the second optical component;

detecting the first optical component and the second optical component to generate a first image data set (T1) corresponding to the first optical component and a second image data set (T2) corresponding to the second optical component; and analyzing the first image data set (T1) and the second image data set (T2) to differentiate the anatomical structures.

36. The method of claim 35, wherein modulating comprises passing one or more of the plurality of illuminating photons and the plurality of interacted photons through two or more of a plurality of tunable conformal filters, a plurality of multivariate optical elements, a liquid crystal tunable filter, a multi-conjugate filter, an acousto-optic filter, a plurality of multivariate optical elements, and a patterned etalon filter.

37. The method of claim 35, wherein analyzing comprises applying an optical computation to the first image data set (T1) and the second image data set (T2).

38. The method of claim 35, wherein analyzing comprises applying a digital stain to the at least of the first image data set (T1) or the second image data set (T2).

39. The method of claim 35, wherein differentiating anatomical structures comprises differentiating a ureter from surrounding tissue.

40. The method of claim 35, wherein analyzing comprises applying one or more chemometric techniques to the first image data set (T1) and the second image data set (T2), the one or more chemometric techniques being selected from a group consisting of a multivariate curve resolution analysis, a principle component analysis (PCA), a partial least squares discriminant analysis (PLSDA), a k means clustering analysis, a band t entropy analysis, an adaptive subspace detector analysis, a cosine correlation analysis, a Euclidian distance analysis, a partial least squares regression analysis, a spectral mixture resolution analysis, a spectral angle mapper metric analysis, a spectral information divergence metric analysis, a Mahalanobis distance metric analysis, and a spectral unmixing analysis.

41. The method of claim 35, wherein modulating comprises modulating the plurality of illuminating photons.

42. The method of claim 35, wherein modulating comprises modulating the plurality of interacted photons.

43. The intraoperative device of claim 1, wherein the optical signal modulator is further configured to transmit a passband wavelength corresponding to an anomaly in a tissue sample, and the anomaly is cancer.

44. The endoscopic instrument of claim 14, wherein the optical signal modulator is further configured to transmit a passband wavelength corresponding to an anomaly in the biological sample, and the anomaly is cancer.

45. The endoscopic instrument of claim 25, wherein the optical signal modulator is further configured to transmit a passband wavelength corresponding to an anomaly in the biological sample, and the anomaly is cancer.

46. The method of claim 35, wherein the modulating includes transmitting a passband wavelength corresponding to an anomaly in the biological sample, and the anomaly is cancer.

* * * * *